United States Patent [19]
Anderson et al.

[11] Patent Number: 5,810,801
[45] Date of Patent: Sep. 22, 1998

[54] METHOD AND APPARATUS FOR TREATING WRINKLES IN SKIN USING RADIATION

[75] Inventors: R. Rox Anderson, Lexington, Mass.; Edward Victor Ross, Jr., San Diego, Calif.; James C. Hsia, Weston; Kathleen McMillan, Concord, both of Mass.

[73] Assignees: Candela Corporation, Wayland, Mass.; The United States of America as represented by the Secretary of the Navy, Washington, D.C.

[21] Appl. No.: 794,876

[22] Filed: Feb. 5, 1997

[51] Int. Cl.⁶ .................................................. A61B 17/36
[52] U.S. Cl. ...................................... 606/9; 606/2; 606/23
[58] Field of Search .................... 606/9, 2, 1, 20, 606/23, 21

[56] References Cited

U.S. PATENT DOCUMENTS

| 4,672,969 | 6/1987 | Dew | 128/397 |
|---|---|---|---|
| 4,854,320 | 8/1989 | Dew et al. | 128/397 |
| 4,976,709 | 12/1990 | Sand | 606/5 |
| 5,002,051 | 3/1991 | Dew et al. | 128/395 |
| 5,133,708 | 7/1992 | Smith | 606/5 |
| 5,137,530 | 8/1992 | Sand | 606/5 |
| 5,140,984 | 8/1992 | Dew et al. | 128/395 |
| 5,151,098 | 9/1992 | Loertscher | 606/16 |
| 5,304,169 | 4/1994 | Sand | 606/5 |
| 5,334,190 | 8/1994 | Seiler | 606/5 |
| 5,348,551 | 9/1994 | Spears et al. | 606/5 |
| 5,374,265 | 12/1994 | Sand | 606/5 |
| 5,409,479 | 4/1995 | Dew et al. | 606/9 |
| 5,437,658 | 8/1995 | Muller et al. | 606/5 |
| 5,445,146 | 8/1995 | Bellinger | 607/89 |
| 5,464,436 | 11/1995 | Smith | 606/9 |
| 5,484,432 | 1/1996 | Sand | 606/5 |

FOREIGN PATENT DOCUMENTS

WO 95/15134   6/1995   WIPO.

*Primary Examiner*—Michael Powell Buiz
*Assistant Examiner*—Julian W. Woo
*Attorney, Agent, or Firm*—Testa, Hurwitz & Thibeault, LLP

[57] ABSTRACT

A method for treating wrinkles in skin involves the use of a beam of pulsed, scanned or gated continuous wave laser or incoherent radiation. The method comprises generating a beam of radiation, directing the beam of radiation to a targeted dermal region between 100 microns and 1.2 millimeters below a wrinkle in the skin, and thermally injuring collagen in the targeted dermal region. The beam of radiation has a wavelength of between 1.3 and 1.8 microns. The method may include cooling an area of the skin above the targeted dermal region while partially denaturing the collagen in the targeted dermal region. The method may also include cooling an area of the skin above the targeted dermal region prior to thermally injuring collagen in the targeted dermal region.

15 Claims, 2 Drawing Sheets

METHOD AND APPARATUS FOR TREATING WRINKLES IN SKIN USING RADIATION

STATEMENT REGARDING FEDERALLY SPONSORED RESEARCH

This invention was made with Government support under Grant Number N00014-94-1-0927 awarded by the Department of the Navy. The U.S. Government has certain rights in this invention.

FIELD OF THE INVENTION

The invention relates generally to the treatment of wrinkles in human skin using radiation. In particular, the invention relates to a method for treating wrinkles in human skin using a beam of laser or incoherent radiation to cause thermal injury in the dermal region of the skin sufficient to elicit a healing response that produces substantially unwrinkled skin.

BACKGROUND OF THE INVENTION

Undesired wrinkles in skin are commonly seen in dermatologic practice. Wrinkles in skin may be caused by age and by exposure to the sun's ultraviolet rays. Human skin consists mainly of two layers: the top layer of skin known as the epidermis; and the layer beneath the epidermis known as the dermis. The dermis is primarily acellular and is composed of water, the protein collagen, and glycosaminoglycans. Water constitutes approximately 70 percent of the total weight of the dermis. Collagen constitutes approximately 70 percent of the dry weight of the dermis, and glycosaminoglycans constitute between approximately 0.1 and 0.3 percent of the dry weight of the dermis. Collagen and glycosaminoglycans are constantly produced by fibroblasts, a type of connective tissue cell, and degraded by enzymes. Collagen degradation relies primarily on specific proteinases known as collagenases.

Collagen provides the dermis with the majority of its structural integrity. With aging, the amount of dermal collagen decreases and is replaced by the protein elastin. In addition, the remaining collagen tends to be chaotically oriented as compared to the more organized patterns found in youthful skin. Glycosaminoglycans are very hydrophilic, and increased amounts of these carbohydrates are associated with the increased skin vigor found in youthful skin. One major difference between the smooth, supple skin of newborns and the drier, thinned skin of older individuals is the far greater relative amount of glycosaminoglycans found in newborn skin. The glycosaminoglycans found in newborns can bind up to 1000 times their weight in water. As the skin ages and the amount of glycosaminoglycans decreases, the skin may become less hydrated and lose some of the suppleness found in youth. Also, the remaining glycosaminoglycans in photo-aged skin are deposited on the haphazardly arranged elastin fibers which have replaced the collagen fibers. The placement of the remaining glycosaminoglycans may partially account for the weather-beaten appearance of photo-aged skin.

Existing procedures for eliminating or reducing the severity of wrinkles include chemical peels, mechanical abrasion and laser ablation. All of these methods remove the top layer of skin. A new top layer forms during healing. Cosmetic improvement is seen when the skin containing wrinkles is replaced by a new layer of horizontally oriented neocollagen in the superficial dermis. However, all of these methods disrupt and completely remove the epidermis. The resulting open wounds require daily care to optimize wound healing. Epidermal destruction and subsequent healing has several undesirable side effects. These undesirable side effects include prolonged hypopigmentation, hyperpigmentation, erythema and edema. Hyperpigmentation occurs frequently in darker skin types as a result of an inflammatory response of the skin. Hyperpigmentation results in the treated area of the subject's skin turning darker than the surrounding untreated skin. Hyperpigmentation can be slow to clear, sometimes taking up to a year to disappear. Hypopigmentation is attributable to damage to the melanin-producing cells in the skin. While generally transient, hypopigmentation can be permanent, and is cosmetically undesirable while it persists. Also, erythema or redness of the skin may be significant for weeks to months after the procedure, requiring the patients to wear conspicuous amounts of make-up.

A known property of collagen fibers, such as those found in the skin, is that the fibers shrink when elevated to a temperature in the range of 60 to 70 degrees Celsius, which is about 30 degrees Celsius above normal body temperature. Temperature elevation ruptures the collagen ultrastructural stabilizing cross-links, and results in immediate contraction in the collagen fibers to about one-third of their original length without changing the structural integrity of the fibers. One known technique shrinks the collagen fibers in the cornea of the eye to change the shape of the cornea and correct refractive disorders. This technique involves the use of laser energy in a wavelength range of about 1.80 to about 2.55 microns. The laser energy is used to irradiate the collagen in the cornea to elevate the collagen to at least 23 degrees Celsius above normal body temperature and thereby achieve collagen shrinkage. U.S. Pat. Nos. 4,976,709, 5,137,530, 5,304,169, 5,374,265, and 5,484,432 to Sand disclose a technique and apparatus for controlled thermal shrinkage of collagen fibers in the cornea.

However, this technique cannot be effectively used to remove wrinkles in skin by shrinking dermal collagen. The bulk of the shrunken, thermally denatured, collagen fibers do not remain in the skin after treatment with this technique. Unlike the cornea, which is avascular, an aggressive healing response in the skin degrades the denatured collagen in the superficial dermis by collagenases, thereby rapidly eliminating the bulk of the shrunken collagen from the skin.

Additionally, in the 1.80 to 2.55 micron wavelength range, strong absorption of the laser energy by water present in the skin limits the penetration depth of the laser radiation to a small fraction of a millimeter. The depths of thermal injury which can be achieved in skin using the wavelengths in this range are therefore limited to the most superficial layer of the skin. Such superficial injury leads to an inflammatory healing response characterized by prolonged visible edema and erythema, as well as the possibility for long lasting pigmentary disturbances.

SUMMARY OF THE INVENTION

The present invention addresses the foregoing problems and provides a method for inducing remodeling of the skin's extracellular matrix by partially denaturing the dermal collagen deeper in the skin, below the surface, while avoiding injury to the epidermis and upper layers of the dermis. The invention offers numerous advantages over existing dermatologic procedures and devices. The surface of the skin remains intact, thereby avoiding the need for dressing wounds; pigmentary disturbances are minimized; and any inflammatory response to the injury is mild and less visually evident.

In general, the present invention features a method for treating wrinkles in skin, without removing a layer of skin, using a beam of pulsed, scanned or gated continuous wave (CW) laser or incoherent radiation. The method comprises generating a beam of radiation having a wavelength between 1.3 and 1.8 microns, directing the beam of radiation to a targeted dermal region between 100 microns and 1.2 millimeters below a wrinkle in the skin, and thermally injuring the targeted dermal region to elicit a healing response that produces substantially less wrinkles.

More specifically, causing selective thermal injury to the dermis activates fibroblasts which deposit increased amounts of extracellular matrix constituents (i.e., collagen and glycosaminoglycans). These increases in extracellular matrix constituents are responsible for dermal skin rejuvenation and the reduced appearance of wrinkles.

In one embodiment, the beam of radiation causes partial denaturation of the collagen in the targeted dermal region. The partial denaturation of the collagen accelerates the collagen synthesis process by the fibroblasts and the deposition of new glycosaminoglycans, leading to the elimination or a reduction in the severity of the wrinkle. The method may also include cooling the surface of the skin and epidermal tissue above the targeted dermal region while irradiating the skin. The method may also include cooling the surface of the skin prior to irradiating the skin.

In a detailed embodiment, the method also includes stretching the skin along the wrinkle before directing the beam of radiation to the targeted dermal region below the wrinkle. Stretching the skin causes thermal injury to the collagen fibers across the wrinkle, while not affecting the fibers along the wrinkle.

The invention also relates to an apparatus for treating wrinkles in skin. The apparatus includes a radiation source and a delivery system which includes a cooling system. The radiation source generates a beam of radiation having a wavelength between 1.3 and 1.8 microns. The delivery system directs the beam of radiation to a targeted dermal region between 100 microns and 1.2 millimeters below a wrinkle in the skin. The cooling system cools the epidermal tissue above the targeted dermal region to minimize injury to the surface of the skin.

BRIEF DESCRIPTION OF THE DRAWINGS

The foregoing and other objects, features and advantages of the invention will become apparent from the following more particular description of preferred embodiments of the invention, as illustrated in the accompanying drawings. The drawings are not necessarily to scale, emphasis instead being placed on illustrating the principles of the present invention.

DETAILED DESCRIPTION OF THE INVENTION

The present invention contemplates a system and method for removing wrinkles which includes delivering a beam of laser or incoherent radiation to cause sufficient thermal injury in the dermal region of the skin to elicit a healing response to cause the skin to remodel itself, resulting in more youthful looking (i.e., substantially unwrinkled) skin. In particular, thermal injury may be in the form of partial denaturation of the collagen fibers in the targeted dermal region of skin. In one embodiment, the radiation beam has a set of parameter ranges carefully selected to partially denature collagen in the dermis while protecting the epidermis by surface cooling. As a result, a subject treated using the method of the invention is able to have the appearance of wrinkles lessened without damage to the epidermis.

Figure 1:
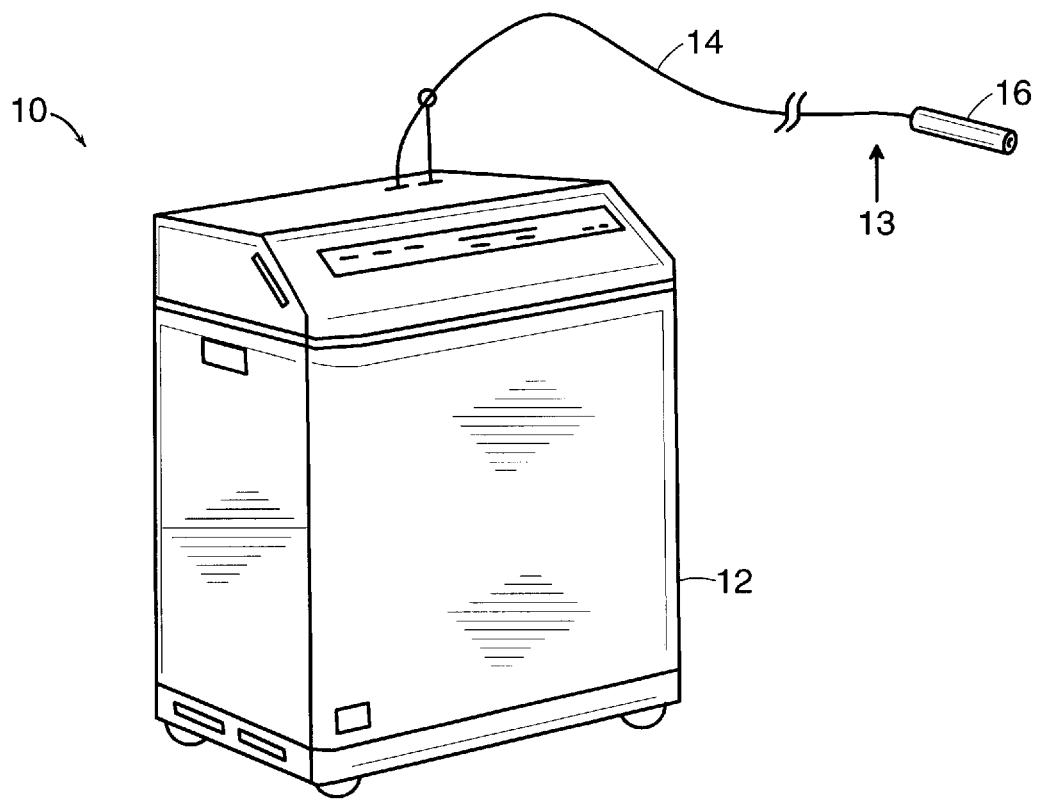
FIG. 1 is an illustration of an apparatus including a radiation source and a delivery system for practicing the invention.

FIG. 1 is an illustration of a system 10 for practicing the invention. The system 10 includes a radiation source 12 and a delivery system 13. A beam of radiation generated by the radiation source 12 is directed to a target region of a subject's skin including a wrinkle via the delivery system 13. In one embodiment, the radiation source 12 is a laser. The laser may generate a beam of pulsed, scanned or gated CW laser radiation. In another embodiment, the radiation source 12 generates incoherent radiation.

The beam of radiation is directed to a targeted dermal region of skin between 100 microns and 1.2 millimeters below the wrinkle. The parameter ranges for the beam have been specifically selected to cause thermal injury to the dermis while avoiding injury to the epidermis and upper layers of the dermis. In particular, the wavelength of the radiation beam has been chosen to maximize absorption in the targeted region of the dermis, and the fluence or power density, depending on the type of radiation, has been chosen to minimize erythema. The wavelength range chosen has a tissue absorption coefficient preferably in the range of about 1 to 20 cm$^{-1}$. Thus, the beam preferably has a wavelength of between about 1.3 and 1.8 microns in one embodiment. Within this wavelength range, radiation energy applied through the surface of the skin is deposited predominantly in the dermal region of the skin. In one embodiment, the radiation beam has a nominal wavelength of approximately 1.5 microns. Lasers which produce radiation having wavelengths in the range of between about 1.3 and 1.8 microns include the 1.33 micron Nd:YAG laser, the 1.44 micron Nd:YAG laser and the 1.54 micron Er:Glass laser. The radiation beam may be pulsed, scanned or gated continuous wave laser radiation. In embodiments having a laser as the radiation source 12, the laser radiation generated preferably has a fluence of between about 10 and 150 joules.

In another embodiment, the radiation used to thermally injure the dermis is incoherent radiation. In embodiments using incoherent radiation, the incoherent radiation generated by the radiation source 12 preferably has a power density of between about 5 and 100 watts per square centimeter.

Figure 2:
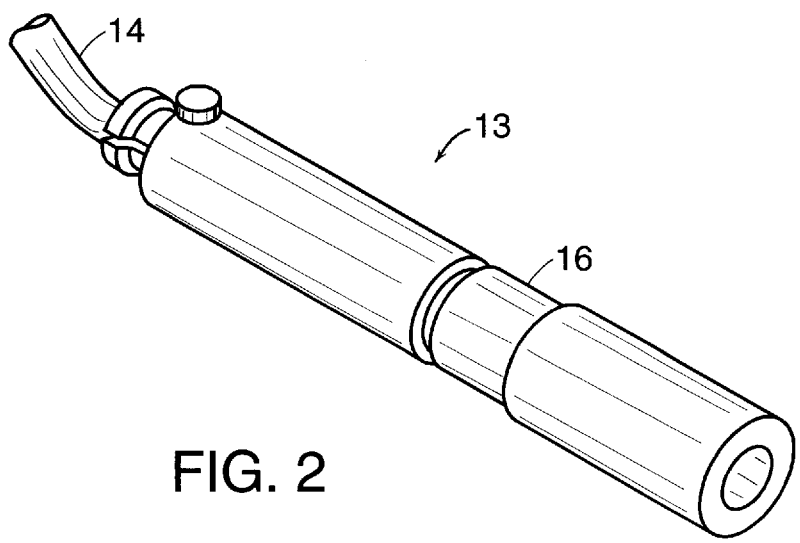
FIG. 2 is an enlarged perspective view of a delivery system incorporating the principles of the invention.

FIG. 2 is an enlarged perspective view of a delivery system 13 incorporating the principles of the invention. The delivery system 13 includes a fiber 14 having a circular cross-section and a handpiece 16. A beam of radiation having a circular cross-section is delivered by the fiber 14 to the handpiece 16. An optical system within the handpiece 16 projects an output beam of radiation to a targeted region of the subject's skin. A user holding the handpiece 16 irradiates the targeted region of the subject's skin including the wrinkle with output pulses from the beam.

Figure 3:
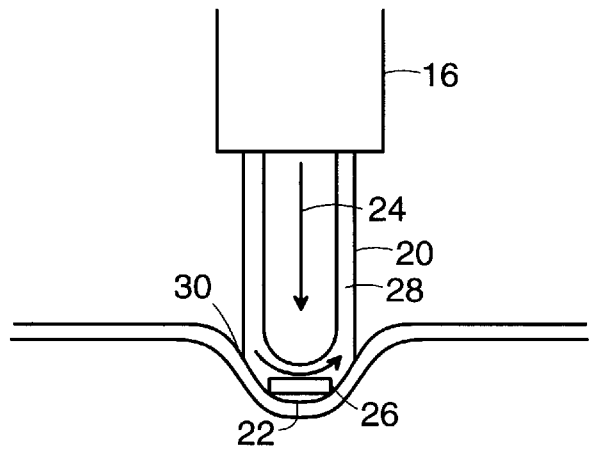
FIG. 3 is an illustration of a wrinkle in skin exposed to a plurality of radiation pulses.

To minimize thermal injury to the epidermis and the upper layers of the dermis, in one embodiment, the delivery system 13 includes a cooling system for cooling the surface of the skin prior to and/or during application of the radiation. In this embodiment, the delivery system 13 is multi-functional and is capable of delivering radiation and cooling the surface of the skin at the same time. FIG. 3 shows one embodiment of a delivery system 13 which includes a cooling system. The handpiece 16 includes a skin contacting portion 20 which is brought into contact with the region of skin 22 receiving the beam of radiation 24. The skin contacting portion 20 cools the epidermal region of skin 22 receiving the beam of radiation. The skin contacting portion 20 includes a sapphire window 26 and a fluid passage 28 which contains a cooling fluid. The cooling fluid may be a fluorocarbon type cooling fluid. The cooling fluid circulates through the fluid passage 28 and past the sapphire window 26 which is in contact with the epidermal region of skin 22 receiving the beam of radiation 24.

In another embodiment, the delivery system 13 and the cooling system are separate systems. The cooling system may comprise a container of a cold fluid. Cooling of the surface of the skin is accomplished by briefly spraying the skin with the cold fluid which extracts heat from the skin on contact. The fluid used can also be a non-toxic substance with high vapor pressure at normal body temperature, such as a freon. These fluids extract heat from the skin by the virtue of evaporative cooling.

FIG. 3 illustrates the treatment of a wrinkle 30 in accordance with the invention. Radiation pulses are produced using the radiation source 12, which may be a pulsed, scanned or gated CW laser or incoherent radiation source. The radiation pulses are directed toward the region 22 of the subject's skin containing the wrinkle 30 by the delivery system 13. The radiation pulses are preferably directed to a targeted dermal region between 100 microns and 1.2 millimeters below the surface of the skin. In a detailed embodiment, the radiation pulses are focused to a region centered at a depth of about 750 microns. The targeted dermal region including a portion of the wrinkle 30 is then irradiated with radiation pulses exiting from the handpiece 16 until collagen in that region is partially denatured. To accomplish this, the collagen at the selected depth in the targeted dermal region is preferably heated to a temperature in the range of about 50 to 70 degrees Celsius. Partially denaturing collagen in the dermis accelerates the collagen synthesis process by the fibroblasts. The thermal injury caused by the radiation is mild and is only sufficient to elicit a healing response and cause the fibroblasts to produce new collagen. Excessive denaturation of collagen in the dermis causes prolonged edema, erythema, and potentially scarring.

The skin contacting portion 20 preferably cools the area of the skin above the targeted dermal region to temperatures below approximately 50 to 70 degrees Celsius during application of the radiation, so as not to cause collateral thermal damage to the epidermis. The radiation beam, due to its wavelength, does not sufficiently penetrate into depths below the targeted dermal region to cause thermal damage deeper in the skin. In one detailed embodiment, the skin contacting portion 20 cools an area of the skin above the targeted dermal region before the radiation is applied. The relative timing of cooling the surface of the skin to applying radiation depends, in part, on the depth to which thermal injury is to be prevented. Longer periods of cooling prior to the application of radiation allow more time for heat to diffuse out of the skin and cause a thicker layer of skin to be cooled, as compared to the thickness of the layer cooled by a short period of cooling. This thicker layer of cooled tissue sustains less thermal injury when the radiation energy is subsequently applied. Continued cooling of the surface of the skin during the delivery of radiation energy extracts heat from the upper layers of the skin as heat is deposited by the radiation, thereby further protecting the upper layers from thermal injury.

The depth of thermal injury caused by the radiation depends primarily on the penetration depth of the radiation used. The penetration depth can be approximated by taking the reciprocal of the absorption coefficient of the skin at the wavelength of the radiation. The thickness of the tissue overlying the zone of injury which is spared from injury depends primarily on the cooling applied prior to and/or during the delivery of radiation energy. By suitably choosing the radiation wavelength, the timing of the surface cooling, the cooling temperature, the radiation fluence and/or the power density as described above, the depth, the thickness and the degree of thermal injury can be confined to a zone within the dermis. These parameters can be chosen to optimally induce the injury required to elicit remodeling within the dermis, while substantially or completely sparing injury to the overlying epidermis and upper layers of the dermis.

In another detailed embodiment, the region of skin including the wrinkle 30 is stretched along the wrinkle 30 before the beam of radiation is directed to the targeted dermal region below the wrinkle 30. Stretching the skin along the wrinkle before irradiating the skin causes partial denaturation of the collagen fibers across the wrinkle, while not damaging the fibers along the wrinkle. Partially denaturing the fibers across the wrinkle tightens the skin sufficiently to cause the wrinkle to disappear.

Figure 4:
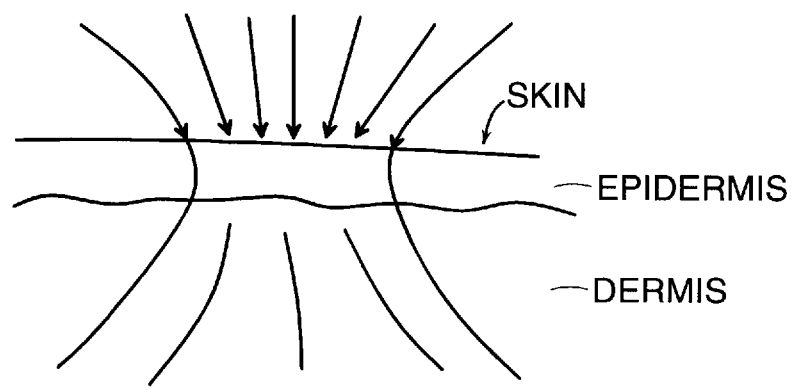
FIG. 4 is an illustration of a region of skin exposed to a highly convergent beam of radiation.

Referring to FIG. 4, in one embodiment, to counteract the effects of scattering, the radiation beam is made highly convergent on the surface of the skin.

EXPERIMENTAL RESULTS

The method of the present invention for treating wrinkles in skin using radiation was applied in a series of in vivo experiments performed on pigs. A pulsed erbium glass laser producing radiation having a wavelength of approximately 1.54 microns was used as the radiation source 12. The laser energy was applied to the pig skin via the skin contacting portion 20 equipped with a cooled sapphire window 26 at the tip, as described above and shown in FIGS. 1–3. The inner surface of the sapphire window 26 was cooled by circulating refrigerated coolant, chilled to approximately minus 25 degrees Celsius through the passage 28. The coolant used was a halocarbon which is transparent to the 1.54 micron laser radiation. The laser beam at the outer surface of the sapphire window 26 was approximately 5 mm in diameter.

The tip of the skin contacting portion 20 was placed in contact with the skin to cool the skin prior to applying the laser radiation. After a set amount of time (hereinafter "the pre-cooling time"), laser energy was applied to the skin. Various combinations of pre-cooling times, laser pulse energies, laser pulse repetition frequencies, time intervals of laser energy delivery, and total number of laser pulses delivered were studied. It was found that by the appropriate choice of these parameters, varying degrees of thermal injury can be achieved at varying depths in the dermis while preserving the viability of the epidermis and upper dermis.

For example, using a pre-cooling time of 5 seconds, a laser energy in the range of between 0.2 and 0.8 joules per pulse at a pulse repetition frequency of 4 Hertz (corresponding to an average laser power in the range between 0.8 to 3.2 watts), and a total of 24 pulses, it was found that varying degrees of thermal injury could be induced in a zone centered at a depth in the range of approximately 0.5 to 1.0 millimeters beneath the surface of the skin, while avoiding injury to the epidermis and upper dermis.

Histology performed on biopsy samples taken at sites treated with the above range of parameters revealed collagen denaturation extending from about 100 microns in the dermis to about 1 mm deep. The epidermis and upper layers of the dermis were preserved as confirmed with nitrotetrazolium blue, a viability stain. In the cases in which only partial collagen denaturation was shown on histology, clinically, the treated areas showed an intact epidermis with mild edema and erythema which resolved completely within two weeks. Histologically, the treated sites showed greatly increased fibroblast activity, new collagen secretion and degradation of denatured collagen. By four weeks post treatment, the treated sites returned to normal, both clinically and histologically.

EQUIVALENTS

While the invention has been particularly shown and described with reference to specific embodiments, it should be understood by those skilled in the art that various changes in form and detail may be made therein without departing from the spirit and scope of the invention as defined by the appended claims.

What is claimed is:

1. A method for treating a wrinkle in human skin, comprising:
    generating a beam of radiation having a wavelength of between 1.3 and 1.8 microns and a fluence of between 10 and 150 joules per square centimeter;
    directing the beam of radiation to a targeted dermal region between 100 microns and 1.2 millimeters below a wrinkle in the skin; and
    causing thermal injury within the targeted dermal region to elicit a healing response that produces substantially unwrinkled skin.

2. The method of claim 1 wherein the wavelength is about 1.5 microns.

3. The method of claim 1 further comprising the step of stretching the skin along the wrinkle before the step of directing the beam of radiation to the targeted dermal region.

4. The method of claim 1 further comprising the step of cooling an epidermal region of the skin above the targeted dermal region contemporaneously with the step of causing thermal injury within the targeted dermal region.

5. The method of claim 4 further comprising the step of pre-cooling the epidermal region of the skin above the targeted dermal region before the step of causing thermal injury within the targeted dermal region.

6. A method for treating a wrinkle in human skin, comprising:
    generating a beam of radiation having a wavelength of between 1.3 and 1.8 microns and a power density of between 5 and 100 watts per square centimeter;
    directing the beam of radiation to a targeted dermal region between 100 microns and 1.2 millimeters below a wrinkle in the skin; and
    causing thermal injury within the targeted dermal region to elicit a healing response that produces substantially unwrinkled skin.

7. The method of claim 6 wherein the wavelength is about 1.5 microns.

8. The method of claim 6 further comprising the step of stretching the skin along the wrinkle before the step of directing the beam of radiation to the targeted dermal region.

9. The method of claim 6 further comprising the step of cooling an epidermal region of the skin above the targeted dermal region contemporaneously with the step of causing thermal injury within the targeted dermal region.

10. The method of claim 9 further comprising the step of pre-cooling the epidermal region of the skin above the targeted dermal region before the step of causing thermal injury within the targeted dermal region.

11. An apparatus for treating a wrinkle in human skin, comprising:
    a source generating a beam of radiation having a wavelength of between 1.3 and 1.8 microns; and
    a delivery system coupled to the source, wherein the delivery system is for directing the beam of radiation to a targeted dermal region between 100 microns and 1.2 millimeters below a wrinkle in the skin, wherein the beam of radiation causes thermal injury to the targeted dermal region sufficient to elicit a healing response that produces substantially unwrinkled skin, the delivery system further comprising:
        a cooling system for contact cooling an epidermal region of the skin above the targeted dermal region, to thereby minimize injury to the epidermal region.

12. The apparatus of claim 11 wherein the delivery system further comprises a fiber coupled to the source, the fiber carrying the beam of radiation; and
    wherein the cooling system further comprises a skin contacting portion having a first end in optical communication with the fiber and a second end, the skin contacting portion projecting the beam of radiation toward the targeted dermal region through the second end of the skin contacting portion.

13. The apparatus of claim 12 wherein the skin contacting portion further comprises a window located at the second end of the skin contacting portion, the window being in optical communication with the fiber; and
    wherein the skin contacting portion has a fluid passage extending across at least a portion of the window, the fluid passage circulating a cooling fluid past the window.

14. An apparatus for treating a wrinkle in human skin, comprising:
    a source generating a beam of radiation having a wavelength of between 1.3 and 1.8 microns;
    a delivery system coupled to the source, wherein the delivery system is for directing the beam of radiation to a targeted dermal region between 100 microns and 1.2 millimeters, below a wrinkle in the skin, wherein the beam of radiation causes thermal injury to the targeted dermal region sufficient to elicit a healing response that produces substantially unwrinkled skin; and
    a cooling system for cooling an epidermal region of the skin above the targeted dermal region, to thereby minimize injury to the epidermal region.

15. The apparatus of claim 14 wherein the cooling system comprises a container of cold fluid, wherein the cold fluid can be sprayed onto the skin to extract heat from the skin on contact.

* * * * *